United States Patent [19]

Margolis

[11] Patent Number: 5,650,055

[45] Date of Patent: Jul. 22, 1997

[54] ELECTROPHORESIS SEPARATION METHOD AND APPARATUS USING BARRIER SEPARATION AND POLARITY REVERSING

[76] Inventor: Joel Margolis, 23 Valley View Crescent, Greenwich NSW 2065, Australia

[21] Appl. No.: 535,126

[22] PCT Filed: Apr. 7, 1994

[86] PCT No.: PCT/AU94/00172

§ 371 Date: Nov. 16, 1995

§ 102(e) Date: Nov. 16, 1995

[87] PCT Pub. No.: WO94/22904

PCT Pub. Date: Oct. 13, 1994

[30] Foreign Application Priority Data

Apr. 7, 1993 [AU] Australia ................. PL8221
Apr. 15, 1993 [AU] Australia ................. PL8285

[51] Int. Cl.⁶ .................................................. G01N 27/26
[52] U.S. Cl. ..................... 204/518; 204/519; 204/450; 204/456; 204/600; 204/606; 204/607; 204/457; 204/608
[58] Field of Search ........................ 204/457, 450, 204/518, 519, 600, 607, 608, 641, 456, 606, 627

[56] References Cited

U.S. PATENT DOCUMENTS

| | | |
|---|---|---|
| 3,029,196 | 4/1962 | Matz et al. . |
| 3,305,471 | 2/1967 | Von Muenchhausen et al. . |
| 3,495,541 | 2/1970 | Natelson . |
| 3,506,554 | 4/1970 | Broome .................. 204/457 |
| 3,720,593 | 3/1973 | Juhos . |
| 5,078,853 | 1/1992 | Manning et al. ............ 204/616 |
| 5,133,844 | 7/1992 | Stevens . |

FOREIGN PATENT DOCUMENTS

| | | |
|---|---|---|
| 6540286 | 9/1985 | Australia . |
| 1628088 | 5/1988 | Australia . |
| 0396053 | 4/1990 | European Pat. Off. . |
| 2270267 | 5/1975 | France . |
| 1046370 | 5/1953 | Germany . |
| 8700635 | 1/1987 | WIPO . |

OTHER PUBLICATIONS

Preparative Biochemistry, 14(3), pp. 205–221, 1984 no month available.
CAS abstract of Yamagishi et al., Quaternary Structure of Limnodrilus Hemoglobin, J. Mol. Biol. (1966), 21(3), 467–72 1966.

(List continued on next page.)

*Primary Examiner*—T. Tung
*Assistant Examiner*—Alex Noguerola
*Attorney, Agent, or Firm*—Michael J. Striker

[57] ABSTRACT

The method and apparatus for preparative electrophoresis is especially useful for proteins. An electrophoretic potential with an initial polarity is applied across an electrophoretic medium (13) to induce at least two species of macromolecules (1,2) in a mixture (3) with a first electrolyte solution to move into the medium (13) and towards a second electrolyte solution on an opposite side of the medium (13). The at least two species of macromolecules (1,2) have similar transport properties, although at least one (1) of the species moves through the medium (13) at a faster rate than the other species (2). The initial polarity is maintained until just before any of the other species of macromolecules have emerged into the second electrolyte solution whereupon the polarity of the electrophoretic potential is reversed while preventing the proportion of the at least one species of macromolecules (1) which has already emerged into the second electrolyte solution from being drawn back into the medium (13). The application and reversal of the electrophoretic potential is repeated until a desired proportion of the at least one species of macromolecules (1) has been transferred to the second electrolyte solution. Preferably, the ratio of the duration of the initial to reversed polarity is between 1:2 and 1:4 so that the at least one other species of macromolecules is substantially completely driven back into the first electrolyte solution.

11 Claims, 2 Drawing Sheets

OTHER PUBLICATIONS

CAS abstract of Carelli et al., Drug Release from Silicone Elastomer through Controlled Polymer Cracking: an Extension to Macromolecular Drugs, Int. J. Pharm. (1989), 50(3), 181-8 1989.

CAS abstract of Yamagishi et al., Quarternary Structure of Limnodrilus Hemoglobin, J. Mol. Biol. (1966), 21(3), 467-72 1966.

Pp. 116 of Webster's II New Riverside University Dictionary, Riverside Publishing Company 1994.

ELECTROPHORESIS SEPARATION METHOD AND APPARATUS USING BARRIER SEPARATION AND POLARITY REVERSING

FIELD OF THE INVENTION

The present invention relates Co a method of, and apparatus for, preparative electrophoresis and, in particular, to such methods and apparatus useful in large scale recovery of macromolecules such as proteins.

DESCRIPTION OF PRIOR ART

Electrophoretic separation of macromolecule such as proteins, peptides, nucleic acids and Other compounds is typically carried out using a medium such as a chemical gel or a membrane. The process involves bringing a first buffer containing a mixture of macromolecule species into contact with the electrophoretic medium whilst an electrophoretic potential is applied along or across the medium so that at least some of the macromolecules are induced to migrate into the medium. The medium typically has a cut-off pore size which is Selected so as to allow the entry of molecules having less than a given size. Further, manipulation of the pH of the buffers used in the separation process can contribute to the selection of the molecule species to be separated. The separated molecules are normally caused to emerge from the medium into a second buffer for collection.

A known problem with such electrophoretic separation method is that molecules larger than the given size will foul the surface of the electrophoretic medium.

This problem has been overcome by a technique of intermittently reversing the polarity of the electrophoretic potential so as to draw the fouling molecules away from the surface of the medium whilst ensuring that there is Still a Positive movement of the molecules to be separated towards the second buffer. To achieve this, the polarity reversal is typically conducted in short bursts only and the total time of polarity reversal is necessarily a fraction of the time of applying the "forward" polarity of the electrophoretic potential (see Australian Patent specification 601040).

Typically, the reversal of the polarity is carried out repeatedly at a rate such that the membrane is constantly being cleared of any surface fouling material. As such, it will be appreciated that the polarity reversal process is analogous to vibrating a sieve. In this model all undersize particles Pass through the sieve but oversize particles clog it. Vibrating the sieve clears the oversize particles away from The surface of the sieve and allows more undersize particles to pass through it.

The known electrophoretic separation methods are generally effective for separating macromolecules having different transport Characteristics (i.e. size, charge, shape, isoelectric point) which have actually entered the electrophoretic medium. Where, however, the transport characteristics of two or more of the macromolecules in the medium are similar, it can be difficult to achieve a complete separation of one of the macromolecular species in the mixture from the others using such conventional methods.

The extent to which two molecule species can be physically separated in an electrophoretic medium will depend not only on their charge characteristics but also on the mean length of paths that the molecules may follow through the electrophoretic medium. Even for a very long mean path length there may not be complete separation of the molecule species due to molecules of The faster moving species being trapped in the medium and contaminating the slower moving molecular species. Even if merely lengthening the medium would achieve complete separation of two species that have similar transport characteristics, the use of such an elongate electrophoretic medium would be inconvenient and there may be practical problems to overcome, such as heat dissipation.

In contrast, the present method and apparatus utilizes the observed differential in the rate of progress of components using a selected electrophoretic medium and/or pH of the buffer so that different species of macromolecules can be conveniently and generally completely separated from one another despite similarities in their transport characteristics.

SUMMARY OF THE INVENTION

The present invention provides a method for the electrophoretic separation of at least one species of macromolecules from a mixture with at least one other species of macromolecules by causing the electrophoretic migration of The at least one species of macromolecules from a first electrolyte solution to a second electrolyte solution through an electrophoretic medium separating those solutions, the medium having paths therethrough with a cross-sectional dimension sufficient to allow at least the at least two species of macromolecules in the mixture to pass therethrough and with a mean path length for the movement of molecular through the medium which is very large relative to the effective size of at least one of the species of macromolecules in the mixture, the method comprising:

applying an electrophoretic potential across the electrophoretic medium with an initial polarity to drive the macromolecules of the mixture into the medium until a proportion of the at least one species of macromolecules emerges from the medium into the second electrolyte solution and the other species of macromolecules have penetrated a substantial distance through the medium but before the other species of macromolecules have so emerged;

reversing the polarity of the electrophoretic potential so as to drive the macromolecules which are in the medium back towards the first electrolyte solution while substantially preventing the proportion of the at least one species of macromolecules that has emerged into the second electrolyte solution from being drawn back into the medium; and repeating the application and reversal of the electrophoretic potential until a desired proportion of the at least one species of macromolecules has been transferred to the second electrolyte solution Preferably, the step of reversing the polarity of the electrophoretic potential is continued or a sufficient time to allow the other species of macromolecules to be substantially completely driven back into the first electrolyte solution before re-establishing the polarity of the electrophoretic potential and repeating the cycle of application and reversal of the Polarity of the electrophoretic potential.

Preferably, the proportion of the one species macromolecules that has emerged into the second electrolyte solution is substantially prevented from being drawn back into the medium by selectively replacing the second electrolyte solution with Fresh second electrolyte solution during the step of reversing the polarity of the electrophoretic potential.

Preferably, the proportion of the at least one species of macromolecules that has emerged into the second electrolyte solution is transported to a first downstream reservoir during the step of applying the initial polarity of the electrophoretic potential and wherein, during the step of reversing the polarity of the electrophoretic potential, a second downstream reservoir supplies the fresh second electrolyte solution.

The reverse polarity of the electrophoretic potential is preferably maintained for a time that is at least equal to no more than the time that the initial polarity maintained. More preferably the ratio of the times of the initial and reverse polarities is from 1:2 to 1:4.

The electrolyte solutions are preferably formulated buffers to keep the electrophoretic medium at a desired pH. Alternatively, this may be achieved by the incorporation of immobilised amphoteric buffering compounds into the electrophoretic medium.

The length of the mean path for the molecule through the electrophoretic medium is preferably at least 10,000 times, and more preferably an least 20,000 times, as long as the effective size of the one species of macromolecules. The effective size of the macromolecules is the maximum size measured in the direction of movement of the macromolecule through the electrophoretic medium under the applied potential serving to draw the macromolecules through the medium. Typically, the length of the mean path, which will of course normally be somewhat longer than the thickness of the electrophoretic medium, will be extremely large relative to the effective size of the macromolecules. The measurement of the effective size of the molecules or of the mean path length are thus not normally matters of critical importance. It would require the elecrophoretic medium to be a membrane of extreme thinness before the matter became critical.

The present invention also provides apparatus for the electrophoretic separation of at least one species of macromolecules from a mixture containing at least one other species of macromolecules, comprising:

a first electrolyte solution compartment to contain the mixture and a first electrolyte solution;

a second electrolyte solution compartment to contain an electrolyte solution for collecting the one species of macromolecules;

an electrophoretic medium Separating the first and second compartments, the medium having pores of a cross-sectional dimension sufficient to allow the macromolecules to pass therethrough and having a mean path length for molecules passing through the medium which is very large relative to the effective size of the macromolecules of at least one of the species of macromolecules in the mixture;

first and second electrodes on opposite sides of the medium for applying an electrophoretic potential across the medium with an initial polarity to induce the macromolecules to move from the first electrolyte solution compartment into the medium and towards the second electrolyte solution compartment;

control means which reverses the polarity of the electrophoretic potential at a first predetermined time after applying the initial polarity of the electrophoretic potential, which first predetermined time is after a proportion of the at least one species of macromolecules have emerged into the second electrolyte solution compartment and before any of the other species of macromolecules have so emerged; which re-establishes the initial polarity of the electrophoretic potential after a second predetermined time which is sufficient to cause the macromolecules which are in the medium to migrate back towards the first electrolyte solution compartment a predetermined distance; and which repeats the application and reversal of the polarity of the electrophoretic potential for a predetermined period until a desired proportion of the one species of macromolecules has been transferred from the mixture to the electrolyte solution in the second compartment.

Preferably, the second predetermined time is sufficient to cause substantially all of the macromolecules which are in the membrane to migrate back into the first electrolyte solution compartment. Preferably, the second predetermined time is at least equal to the first predetermined time. More Preferably, the ratio of the first predetermined time to the second predetermined time is from 1:2 to 1:4.

Preferably, the control means also causes the second electrolyte solution compartment to fluidly communicate with a first downstream reservoir during the step of applying the initial polarity of the electrophoretic potential so as to collect the electrolyte solution containing the separated macromolecules of the one species of macromolecules, and automatically disconnects the second compartment from the first downstream reservoir and connects it no a second downstream reservoir which supplies a fresh electrolyte solution to the second compartment during the step of reversing the polarity of the electrophoretic potential.

Preferably, the predetermined period is sufficient to remove a significant proportion, preferably at least 40% and more preferably at least 50% of the at least one species of macromolecules from the mixture and concentrate same in the electrolyte solution in the second compartment and first downstream reservoir.

In one preferred embodiment, the apparatus includes a plurality of mediums arranged in a series having decreasing pore size, each membrane to be used to separate a respective species of macromolecules from the mixture.

In the same way that the prior art arrangement involving reversal of polarity could be likened to vibrating a sieve, the process according to the present invention can be likened to a fun-run. Using the fun-run analogy, the present invention is like separating male runners from female runners with the knowledge that on average, male runners are ranter than female runners. A large group containing a mixture of male and female runners is assembled at the start line with this race course (i.e. from start to finish) being analogous to the electrophoretic medium of the present invention. The race is then started with male and female runners racing towards the finish line. It can be predicted that a certain number if male runners will finish the fun-run before any of the female runners. The fun-run is purposely stopped just prior to any female runners crossing the finish line. All of the runners which have not yet crossed the finish line would then be sent back to start another race. The fun-run races can then be repeated until a desired proportion of the male runners have been separated from the female runner.

BRIEF DESCRIPTION OF THE DRAWINGS

A preferred form of the present invention will be described by way of example with reference to the accompanying drawings, wherein.

BEST METHOD OF CARRYING OUT THE INVENTION

Figure 1:
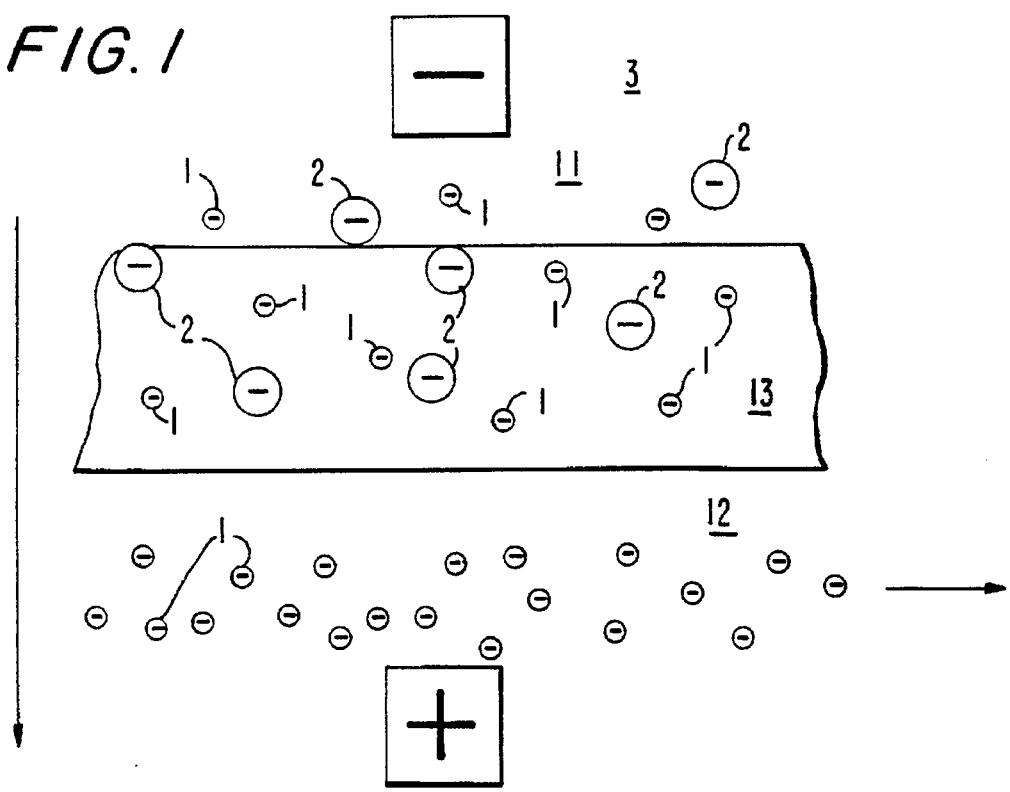
FIGS. 1 and 2 are schematic views of the electrophoretic separation process of the present invention at two separate stages of the process.
Figure 2:
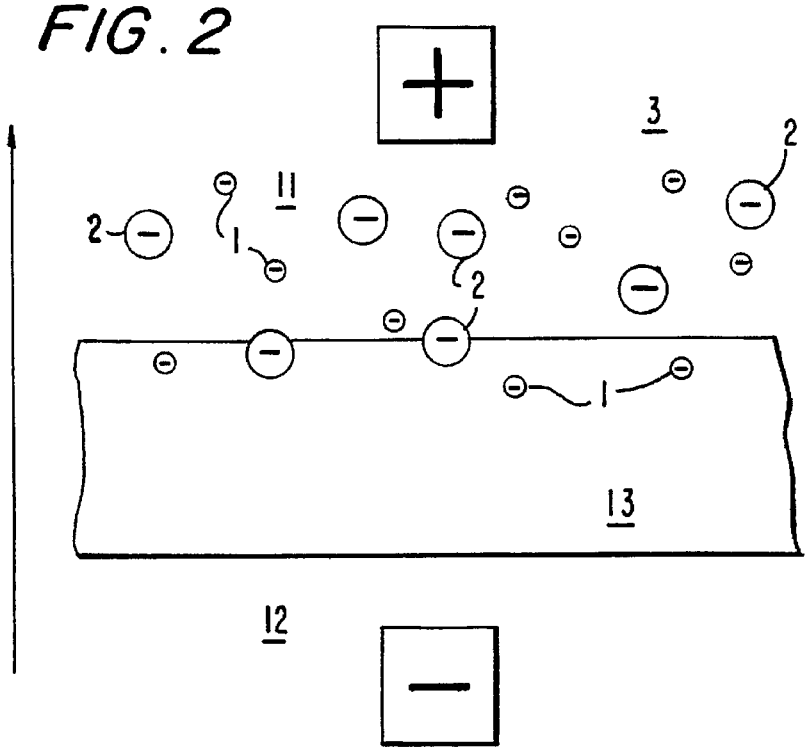
Figure 3:
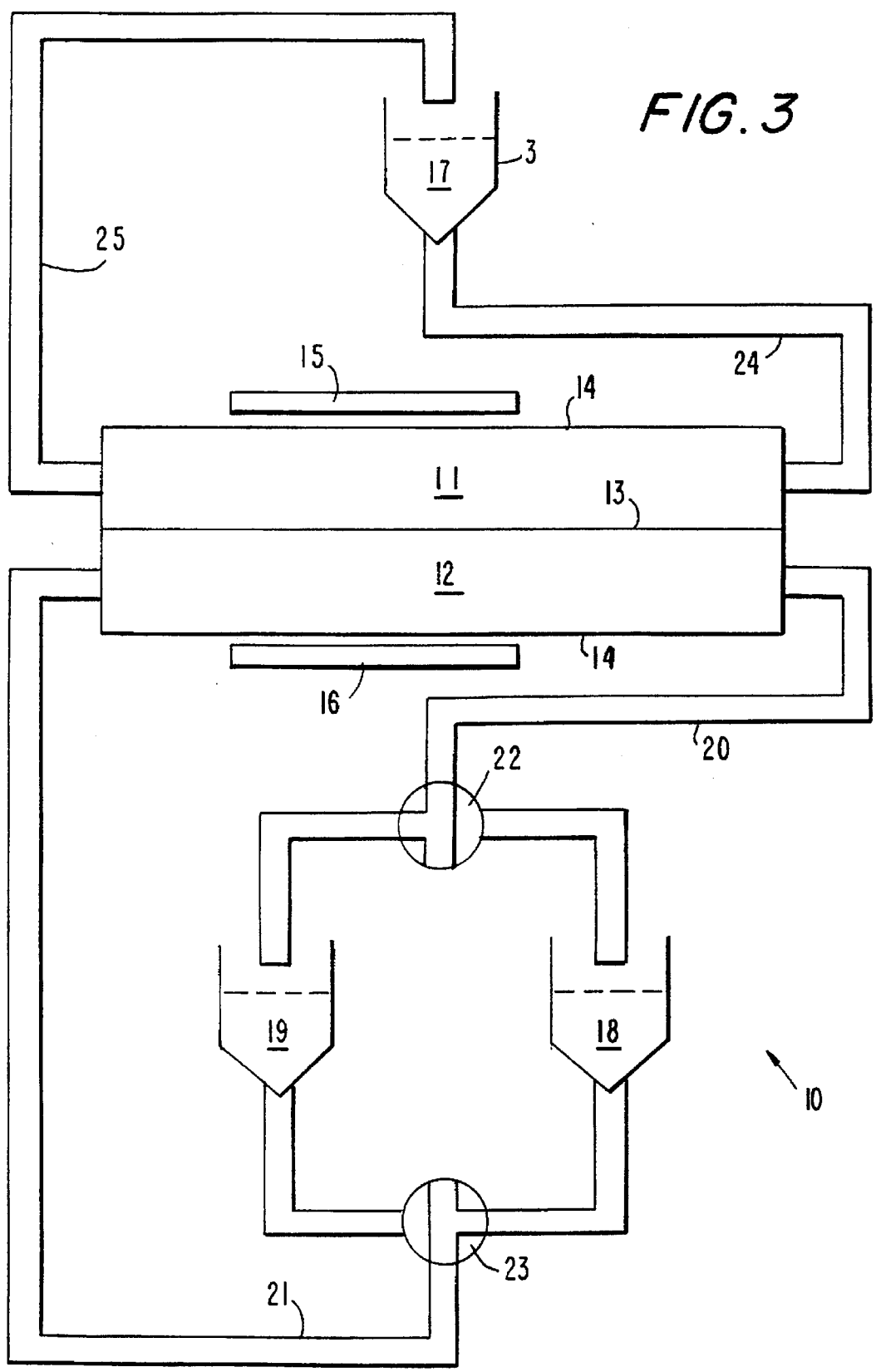
FIG. 3 is a schematic view of the electrophoretic separation apparatus of the present invention.

The apparatus 10 shown in FIG. 3 includes an upstream buffer compartment 11 and a downstream buffer compartment 12 separated by an electrophoretic membrane 13. The compartments 11, 12 have outer walls 14 which are permeable to ion solutions but not to macromolecules such as protein.

Electrodes 15, 16 are provided outside the upstream and downstream compartments 11, 12 so as to be on opposite sides of the membrane 13. The electrodes 15, 16 are used to apply an electrophoretic potential across the membrane 13.

The first compartment 11 communicates via tubes 24, 25 with art upstream reservoir 17 so that commercial quantities of a mixture containing various species of macromolecules can be circulated as a first buffer stream past the membrane 13. The mixture 3 contains a predetermined species 1 of macromolecules which is desired to be separated from other specie(s) 2 of macromolecules having similar transport characteristics which is/are also contained in the mixture 3.

The downstream compartment 12 selectively communicates via tubes 20, 21 with either a first downstream reservoir 18 or a second downstream reservoir 19 which are arranged in parallel. The first downstream reservoir 18 is used to collect buffer containing the one species of macromolecules which has been separated from the mixture, and the second downstream reservoir 19 contains a fresh aliquot of buffer solution The downstream reservoirs 18, 19 are connected to the tubes 20, 21 by a pair of control valves 22, 23 so that control device (not shown) can fluidly connect one or the other of the reservoirs 18, 29 to the downstream compartment 12.

In use, the mixture 3 containing the two or more species of macromolecules 12, including a particular species of macromolecules 1 which is to be separated from the mixture 3, is contained in the upstream reservoir 17 and is circulated as a first buffer stream through the tube 24, the upstream compartment 11 and back to the reservoir 17 through the tube 25.

The membrane 13 is selected having a predetermined pore size so that the species of macromolecules 1 which is to be separated from the mixture 3 will progress through the membrane 13 at a faster rate than any of the other species of macromolecules 2 in the mixture. A suitable electrophoretic potential is applied across the membrane 13 by means of the electrodes 15, 16 with an initial polarity for inducing the macromolecules 1, 2 to migrate from the mixture in the upstream compartment 11 into the membrane 13 and towards the downstream compartment 12.

The initial polarity of electrophoretic potential is maintained whilst the species of macromolecules 1 to be separated moves through the membrane 13 and emerges into the downstream compartment 12 and for so long as substantially none of the other species of macromolecules 2 have emerged into the downstream compartment 12. In this phase of the process, the first downstream reservoir 18 is caused to be connected to the downstream compartment 12 so that the separated species of macromolecules 1 can be collected.

At a first predetermined time when the other species of macromolecules 2 are about to emerge from the membrane 13 into the downstream compartment 12, the polarity of the electrophoretic potential is reversed so as to induce all of the macromolecules 1, 2 within the membrane 13 to migrate back towards the upstream compartment 11. The reversed polarity of the potential is maintained for a second predetermined time until substantially all of the macromolecules 1, 2 have emerged from the membrane 13 back into the upstream compartment 11 whereupon the initial polarity is re-established to a new cycle.

During the reversed polarity phase of the process, the second downstream reservoir 19 is caused to be connected to the downstream compartment 12 so as to supply a fresh aliquot of buffer solution into the downstream buffer compartment 12. In this way, the proportion of the species of macromolecules which has already emerged from the membrane 13 into the downstream solvent stream is moved out of the downstream compartment 12 and replaced with the fresh aliquot of buffer solution. This generally avoids any of the one species of macromolecules which have already been separated from being induced back into the membrane 13.

The above process can be repeated on the mixture using a series of membranes 13 having different pore sizes and/or by changing the pH of the buffer so as to successively separate different species of macromolecules contained in the mixture. For example, the membrane 13 for each successive stage of the separation process have decreasing pore size to create a discontinuous pore gradient.

It will be appreciated that the selection of the membrane, the buffer, and the above first and second predetermined times for applying and reversing the electrophoretic potential must first be determined by trials using, for example, coloured markers. Once the most appropriate membrane and buffer solution for separating a particular species of macromolecules from a particular mixture have been selected, and the times for applying the electrophoretic potential and reversing the polarity of the potential respectively have been determined for the selected membrane and buffer, the process can be easily automated using appropriate control devices.

Further, the cycle of applying and reversing the electrophoretic potential in accordance with the present invention will also serve to "flush out" any macromolecules which foul the surface of the membrane 13.

EXAMPLE

The apparatus described in FIG. 3 was used for the separation of stained Lysozyme monomer (MW 14 kD) from dimer (28 kD) and higher polymers from a mixture thereof. The buffer used in the first and second buffer compartments was Tris-Borate-EDTA an a concentration of 50 mM giving a buffered pH of 8.3.

The electrophoretic media comprised a stack of four membranes each having a molecular weight exclusion of approximately 50 kD. The total thickness of 0.4 mm. The electrophoretic current was 180 v, 0.4 A with a brief reverse pulse periodically to reduce surface fouling of the membrane.

The apparatus was operated with an initial forward polarity for three minutes followed by a revise polarity for six minutes. It was found this substantially pure monomer was accumulated in the second buffer. When the initial forward polarity was increase to five minutes second buffer solution was found to contain dimer.

It will be appreciated by persons skilled in the art that numerous variations and/or modifications ma be made to the invention as shown in the specific embodiments without departing from the spirit or scope of the invention as broadly described. The present embodiments are, therefore, to be considered in all respects illustrative and not restrictive.

We claim:

1. A method for electrophoretic separation of at least one species of macromolecules from a mixture with at least one other species of macromolecules by causing electrophoretic migration of the at least one species of macromolecules from a first electrolyte solution to a second electrolyte solution through an electrophoretic medium separating said electrolyte solutions, wherein neither the first nor the second electrolyte solution has substantial movement through the electrophoretic medium, the medium having paths therethrough with a cross-sectional dimension that will allow at least the at least one species of macromolecules and the at least one other species of macromolecules in the mixture to pass through the medium and with a mean path length for movement of molecules through the medium which is at least 10,000 times a maximum size measured in direction of movement of at least one of the species of macromolecules in the mixture, the method comprising the steps of:

a) applying an electrophoretic potential across the electrophoretic medium with an initial polarity to drive the macromolecules of the mixture into the medium until a proportion of the at least one species of macromolecules emerges from the medium into the second electrolyte solution and the at least one other species of macromolecules have penetrated a predetermined distance through the medium but before the at least one other species of macromolecules have so emerged;

b) reversing the polarity of the electrophoretic potential so as to drive the macromolecules which are in the medium back towards the first electrolyte solution while substantially preventing the proportion of the at least one species of macromolecules that has emerged into the second electrolyte solution from being drawn back into the medium; and c) repeating the applying reversing of the electrophoretic potential of steps a) and b) until a desired proportion of the at least one species of macromolecules has been transferred to the second electrolyte solution; and d) recycling the first and second electrolyte solutions on either side of the electrophoretic medium in separate flow streams.

2. The method as defined in claim 1, wherein the proportion of the at least one species of macromolecules that has emerged into the second electrolyte solution is transported to a first downstream reservoir during the step of applying the initial polarity of the electrophoretic potential and wherein, during the step of reversing the polarity of the electrophoretic potential, a second downstream reservoir supplies the fresh second electrolyte solution.

3. The method as defined in claim 1, wherein repeating of the cycle of applying and reversing the electrophoretic potential continues until at least 40% of the at least one species of macromolecules is removed from the first electrolyte solution and collected in the second electrolyte solution.

4. The method as defined in claim 1, wherein the mean path length of the electrophoretic medium is at least 20,000 times as long as an effective size of at least one of the at least one species of macromolecules and the at least one other species of macromolecules in the mixture.

5. The method as defined in claim 1, wherein the electrolyte solutions are pH buffers.

6. The method as defined in claim 1, wherein a ratio of the duration of the applying of the electrophoretic potential with the initial polarity and the duration of the reversing of the polarity is from 1:2 to 1:4.

7. An apparatus for electrophoretic separation of at least one species of macromolecules from a mixture containing at least one other species of macromolecules, comprising:

a first electrolyte solution compartment to contain the mixture and a first electrolyte solution;

a second electrolyte solution compartment to contain a second electrolyte solution for collecting the at least one species of macromolecules;

an electrophoretic medium separating the first and second compartments, the medium having paths with a cross-sectional dimension that will allow the macromolecules to pass therethrough and with a mean path length for molecules passing through the medium which is at least 10,000 times a maximum size measured in a direction of movement of the macromolecules of at least one of the species of macromolecules in the mixture, wherein neither the first nor the second electrolyte solution flows through the electrophoretic medium to any substantial extent;

first and second electrodes on opposite sides of the medium for applying an electrophoretic potential across the medium with an initial polarity to induce the macromolecules to move from the first compartment into the medium and towards the second compartment;

means for recycling the first and second electrolyte solutions on either side of the electrophoretic medium in separate flow streams; and control means for reversing the initial polarity of the electrophoretic potential for a first time duration after applying the electrophoretic potential with the initial polarity, which first time duration extends until a proportion of the at least one species of macromolecules have emerged into the second compartment and ends before any macromolecules of the at least one other species of macromolecules have so emerged; and for re-establishing the electrophoretic potential with the initial polarity after a second time duration during which the macromolecules which are in the medium migrate a predetermined distance back towards the first compartment; and for repeating the applying of the electrophoretic potential with the initial polarity and the reversing of the polarity for a time period until a desired proportion of the at least one species of macromolecules has been transferred from the mixture to the second electrolyte solution in the second compartment.

8. The apparatus as defined in claim 7, wherein the second time duration will cause substantially all of the macromolecules which are in the membrane to migrate back into the first electrolyte solution.

9. The apparatus as defined in claim 7, including a plurality of additional mediums arranged in a series of decreasing pore size, each additional medium to be used to separate a respective species of macromolecules from the mixture.

10. A method for electrophoretic separation of at least one species of macromolecules from a mixture with at least one other species of macromolecules by causing electrophoretic migration of the at least one species of macromolecules from a first electrolyte solution to a second electrolyte solution through an electrophoretic medium separating said electrolyte solutions, the medium having paths therethrough with a cross-sectional dimension that will allow at least the at least one species of macromolecules and the at least one other species of macromolecules in the mixture to pass through the medium and with a mean path length for movement of molecules through the medium which is at least 10,000 times a maximum size measured in direction of movement of at least one of the species of macromolecules in the mixture, the method comprising the steps of:

a) applying an electrophoretic potential across the electrophoretic medium with an initial polarity to drive the macromolecules of the mixture into the medium until a proportion of the at least one species of the macromolecules emerges from the medium into the second electrolyte solution and the at least one other species of macromolecules have penetrated to a predetermined distance through the medium but before the at least one other species of macromolecules have so emerged;

b) reversing the polarity of the electrophoretic potential so as to drive the macromolecules which are in the medium back towards the first electrolyte solution while substantially preventing the proportion of the at least one species of macromolecules that has emerged into the second electrolyte solution from being drawn back into the medium;

c) repeating the applying and reversing of the electrophoretic potential of steps a) and b) until a desired proportion of the at least one species of macromolecules has been transferred to the second electrolyte solution.

d) continuing reversing the polarity of the electrophoretic potential for a duration of time that will allow the at least one other species of macromolecules to be substantially completely driven back into the first electrolyte solution before reestablishing the initial polarity of the electrophoretic potential and repeating the cycle of applying and reversing the polarity of the electrophoretic potential; and e) substantially preventing the proportion of the at least one species of macromolecules that has emerged into the second electrolyte solution from being drawn back into the medium by selectively replacing the second electrolyte solution with fresh second electrolyte solution before the step of reversing the polarity of the electrophoretic potential.

11. An apparatus for electrophoretic separation of at least one species of macromolecules from a mixture containing at least one other species of macromolecules, comprising:

a first electrolyte solution compartment to contain the mixture and a first electrolyte solution;

a second electrolyte solution compartment to contain a second electrolyte solution for collecting the at least one species of macromolecules;

an electrophoretic medium separating the first and second compartments, the medium having paths with a cross-sectional dimension that will allow the macromolecules to pass therethrough and with a mean path length for molecules passing through the medium which is at least 10,000 times a maximum size measured in a direction of movement of the macromolecules of at least one of the species of macromolecules in the mixture;

first and second electrodes on opposite sides of the medium for applying an electrophoretic potential across the medium with an initial polarity to induce the macromolecules to move from the first compartment into the medium and towards the second compartment;

control means for reversing the initial polarity of the electrophoretic potential for a first time duration after applying the electrophoretic potential with the initial polarity, which first time duration extends until a proportion of the at least one species of macromolecules have emerged into the second compartment and ends before any macromolecules of the at least one other species of macromolecules have so emerged; and for re-establishing the electrophoretic potential with the initial polarity after a second time duration during which the macromolecules which are in the medium migrate a predetermined distance back towards the first compartment; and for repeating the applying and reversing of the electrophoretic potential with the initial polarity for a time period until a desired proportion of the at least one species of macromolecules has been transferred from the mixture to the second electrolyte solution in the second compartment, the control means also including means for connecting the second electrolyte solution compartment to fluidly communicate with a first downstream reservoir during the step of applying the electrophoretic potential with the initial polarity in order to collect the second electrolyte solution containing separated macromolecules of the at least one species of macromolecules, and means for disconnecting the second compartment from the first downstream reservoir and connecting the second compartment to a second reservoir which supplies fresh electrolyte solution to the second compartment during the step of reversing the polarity of the electrophoretic potential.

* * * * *